United States Patent
Adam

(10) Patent No.: US 11,293,006 B1
(45) Date of Patent: Apr. 5, 2022

(54) ENDOPHYTES FOR ORGANIC NITROGEN USE FOR SUSTAINABLE AGRICULTURE

(71) Applicant: Nadia Adam, Mishawaka, IN (US)

(72) Inventor: Nadia Adam, Mishawaka, IN (US)

(73) Assignee: Biomineral Systems LLC, South Bend, IN (US)

( * ) Notice: Subject to any disclaimer, the term of this patent is extended or adjusted under 35 U.S.C. 154(b) by 124 days.

(21) Appl. No.: 16/939,029

(22) Filed: Jul. 26, 2020

Related U.S. Application Data

(63) Continuation of application No. 14/578,494, filed on Dec. 22, 2014, now Pat. No. 10,836,993.

(51) Int. Cl.
| | | |
|---|---|---|
| *C12N 1/20* | (2006.01) | |
| *C12N 15/82* | (2006.01) | |
| *A01N 63/10* | (2020.01) | |
| *A01H 3/00* | (2006.01) | |
| *C12R 1/01* | (2006.01) | |
| *C12R 1/19* | (2006.01) | |

(52) U.S. Cl.
CPC ............... *C12N 1/20* (2013.01); *A01H 3/00* (2013.01); *A01N 63/10* (2020.01); *C12N 1/205* (2021.05); *C12N 15/8261* (2013.01); *C12R 2001/01* (2021.05); *C12R 2001/19* (2021.05); *Y02P 60/21* (2015.11)

(58) Field of Classification Search
None
See application file for complete search history.

(56) References Cited

U.S. PATENT DOCUMENTS 9,364,005 B2 * 6/2016 Mitter ................ G01N 33/0098

\* cited by examiner

*Primary Examiner* — Vera Afremova

(57) ABSTRACT

Endophytic microbial strains as biocatalysts isolated from fresh plant samples, compositions, and methods of use thereof to enhance the growth and/or yield of a plant in the presence of reduced synthetic nitrogen fertilizers are provided. Endophytic microbial strains serve as biocatalysts to solubilize organic (proteinaceous) nitrogen otherwise unavailable to plants for their nutritional needs. Thus defined, biocatalysts will serve to replace synthetic nitrogen fertilizers. Also provided are materials and methods for inoculating plants with these biocatalysts at carefully selected inoculum densities to reliably reduce the amount of nitrogen fertilizer by 50% thus accomplishing optimal yields in technically and cost-effective manner.

20 Claims, 8 Drawing Sheets

Figure 3

**Table 1. Average Nutrient Analyses (as is)* of Major Types of Manure in Oklahoma**

| Manure Type | Dry Matter % | Total N | $P_2O_5$ | $K_2O$ |
|---|---|---|---|---|
| | | ——— lbs./ton ——— | | |
| Feedlot Manure | 62 | 24 | 21 | 25 |
| Broiler Litter | 77 | 63 | 61 | 50 |
| | | ——— lbs./1000gal ——— | | |
| Lagoon Effluent | 0.5 | 4.2 | 1.0 | 5.0 |
| Lagoon Sludge | 7 | 15 | 16 | 11 |
| Dairy Slurry | 3 | 13 | 11 | 11 |

*$P_2O_5$ and $K_2O$ are commonly used for fertilizer ingredients instead of P and K. Some laboratories may still report in elemental P and K content. To convert, use the following equations: $K_2O = K \times 1.2$ or $P_2O_5 = P \times 2.29$

ENDOPHYTES FOR ORGANIC NITROGEN USE FOR SUSTAINABLE AGRICULTURE

FIELD OF THE INVENTION

The present invention relates to the field of sustainable agriculture. Specifically, the disclosure provides microbial compositions and methods useful for the optimal production of crop plants in the absence of synthetic nitrogen fertilizers or in the presence of synthetic nitrogen fertilizers applied at the rate of 30-50% less than needed. In particular, the compositions and methods disclosed herein are useful for enhancing plant growth in the complete absence of synthetic nitrogen fertilizers or in their much reduced presence.

BACKGROUND OF THE INVENTION

The United States is, by far, the largest producer of corn in the world, producing as much as 35% of world's corn, 33% of world's soybean, more than 65% of world's sorghum and is the biggest wheat exporter (Ag 101, US EPA).

Nitrogen (N) is an essential plant macronutrient; of the three essential macronutrients (N, P, and K), nitrogen is required by plants in the greatest amount and its availability is a major factor limiting growth of plants in natural as well as in agricultural soils (Kraiser et al., 2011). A simplified view of the nitrogen cycle in soils is shown in FIG. 1.

Nitrogen (N) is present in the biosphere in various chemical forms with molecular nitrogen gas ($N_2$) representing 80% of its atmospheric composition (Sanhueza, 1982). Plants however, cannot directly use this form of N. Nitrogen therefore, enters the biological cycle as ammonia/ammonium (either via biological fixation i.e., prokaryotic conversion of $N_2$ to ammonia or production of ammonia by the Haber-Bosch industrial fixation of $N_2$ as mentioned above) and as atmospheric nitrate (Mannheim et al., 1995). Once N is fixed as nitrate or ammonia, it can have two main fates: (i) nitrate and ammonia can undergo biochemical processes that transform them back to $N_2$ (Mannheim et al., 1995); or they can be reduced and/or assimilated for the biosynthesis of N-containing metabolites such as proteins/peptides. These metabolites (amino acids, urea, small polypeptides) and other N-containing biomolecules can then be released back to the environment by secretion, excretion, or by the decay of organic matter (Jones et al., 2005a).

Historically, the classical paradigm of the terrestrial N cycle has asserted that organic N must be converted into inorganic N ($NO_3$—N, $NH_4$—N) by soil microorganisms prior to becoming available to plant roots, and thus N mineralization (ammonification) has been viewed as the bottleneck in plant N nutrition (Warren and Adams, 2007). Therefore, synthetic N fertilizers applied to support crop growth have always been in the form of ammonium or nitrates.

Previous to the discovery of the Haber Bosch process almost 100 years ago to convert atmospheric $N_2$ to $NH_3$, food production was always limited by the ability to supplement soil nitrogen by crop rotation, leaving the soil fallow or applying manure. However, with cheap production of synthetic N fertilizers, anhydrous ammonia, urea, and urea ammonium nitrate (UAN)—widely used by the US farmers; synthetic N fertilizers have become 'key' to phenomenal increases in crop yields thus promoting agricultural intensification in the US and around the world.

This increase however, has come at a high cost to the environment. For example, Chesapeake bay, the nation's largest estuary is polluted from agricultural operations whose nitrogen (and P) runoff from the synthetic fertilizers applied to the farm fields fills the bay water causing eutrophication, fish kills, and proliferations of human pathogenic bacteria (www.grist.org, 2010*). In the gulf of mexico which drains the US heartland and the upper Midwest, a deadzone is produced almost the size of 5000-8000 sq. miles in the summer months impacting fisheries along the gulf's borders in Texas, Louisiana, Mississippi, Alabama, and Florida (www.grist.org, 2010*).

The Haber-Bosch process to convert $N_2$ to $NH_3$ requires high temperatures and pressures and is very energy intensive so much so that ~1% of the global energy consumption is required to produce synthetic ammonia for N fertilizer. Therefore, there is a strong correlation between the price of natural gas and oil and fertilizer prices (www.grist.org, 2010*).

The US consumes nearly 12% of the global annual synthetic N fertilizer mostly from declining natural gas reserves and is going to be increasingly dependent on imports from foreign nations such as Trinidad and Tobago, Canada, Russia and Ukraine for its synthetic N fertilizer needs (www.grist.org, 2010*).

Currently, US is able to produce only 45% of its nitrogen fertilizer needs and is tightly consolidated by only 3 to 4 companies namely, CF industries, Terra, and Agrium that are also amongst the nation's largest environmental polluters (www.grist.org, 2010*).

* http://www.grist.org/article/series/the-n2-dilemma-is-america-fertilizing-disaster Of the applied N fertilizer, only 30-50% is actually taken up by plants. Recent research has shown that this over-application of synthetic N fertilizer although a quick fix for supplying plant needs also causes overgrowth of bacteria and fungi. According to one line of research, overgrowth of microorganisms in turn could potentially oxidize soil organic carbon critical to maintaining soil quality and the ability to retain soil N thus possibly priming the soils to need progressively more and more of the 'same quick fix' to maintain consistent crop yields (Mulvaney et al., 2006; Mulvaney et al., 2007; Khan et al., 2007; Mulvaney et al., 2009; Mulvaney et al., 2010a; Mulvaney et al., 2010b).

The over-application of N fertilizer also has significant adverse human health effects through leaching of nitrates in the ground water causing methemoglobinemia in infants and reacting with other chemicals in the body to produce N-nitroso compounds that have been linked to birth defects and cancer via model animal studies.

From the economic perspective, although the US currently leads the world in corn production, the portion of agricultural revenue returned to farmers decreased from 37% to 19% from 1950 to 2002 (Atwell et al., 2010). In addition, input costs increased sevenfold and the real price of corn adjusted for inflation decreased fivefold (Duffy, 2006).

All the above unequivocally show that corn production in particular and crop production in general is unsustainable from all perspectives, including environmental, soil quality, economic, and human health. Hence, invention for a sustainable, cost effective, and similarly reliable alternative to synthetic N fertilizers is critical to maintaining intensive agriculture, global food security, and mitigating the effects of global climate change.

The premise of applying synthetic N fertilizer as $NH_4^+$ and nitrate was based on the conventional wisdom that plants can take up nitrogen in only these forms. However, recent research has shown that in addition to taking up these inorganic forms of nitrogen, uptake of organic nitrogen in the form of oligopeptides and free amino acids is also a major uptake pathway in plants (Jones et al., 2005a; Jones et al., 2005b; Adamcyzk et al., 2009; Kraiser et al., 2011).

Although, historically, the classical paradigm of the terrestrial N cycle has asserted that organic N must be converted into inorganic N ($NO_3$—N, $NH_4$—N) by soil microorganisms prior to becoming available to plant roots, with N mineralization (ammonification) as the bottleneck in plant N nutrition (Warren and Adams, 2007) soil N is dominated by organic forms and approximately 40% of total soil N is present in the form of polymers such as proteins and peptides (Schulten and Schnitzer, 1997).

Recent research has shown that plants can indeed take up organic nitrogen when liberated from soil polymers such as amino acids bound in peptides and proteins (Jones et al., 2005a; Jones et al., 2005b; Adamcyzk et al., 2009; Kraiser et al., 2011). Several amino acid transporters have been identified in plants such as lysine-histidine transporter 1 (LHT1), amino acid permease 1 (AAP1), and amino acid permease 5 (AAP5) in the roots of *Arabidopsis thaliana* (Hirner et al., 2006; Lee et al., 2007; Svennerstam et al., 2008).

Plants can access N in soil proteins using proteases in root exudates (Paungfoo-Lonhienne et al., 2008). In addition, bacteria colonizing plant roots and known to have a beneficial effect on plant growth (referred to as PGPB aside from the bacteria that fix atmospheric $N_2$) also exude extracellular enzymes such as phosphatases and proteases for respectively, P and N nutritional needs of plants (Kraiser et al., 2011; Ahearn et al., 1968; Gupta et al., 2002).

The de-polymerization of these compounds by enzymes such as proteases creates short peptides and free amino acids (Jamtgard et al., 2010). These free amino acid (FAA) reserves in soils are mostly higher than ammonium and nitrate and offer the largest and most reliable source of FAAs (Lipson and Näsholm, 2001). The bound amino acids (BAAs) for example those in proteins and peptides in soils were significantly higher than mineral-N in unfertilized soil solutions as shown in FIG. 2 except lettuce grown in farm land which had been fertilized with synthetic N fertilizers (Jamtgard et al., 2010).

Indeed field studies have shown evidence for direct uptake of amino acids by plants in diverse ecosystems such as Alaskan tussock tundra, boreal coniferous forest, heathland, subtropical rainforest, and agricultural land further underlining the importance of organic protein-N for plant nutrition (Kielland, 1994; Näsholm et al., 1998; Stribley and Read, 1980; Schmidt and Stewart, 1999; Jones and Darrah, 1994; Yamagata and Ae, 1996; Näsholm et al., 2001; Sauheitl et al., 2001). Direct uptake of N was also shown recently by Tida et al., (2009) in tomato seedlings using $^{15}NH_4Cl$, $K^{15}NO_3$, 1, 2-$^{13}C_2$ $^{15}N$-glycine labeling techniques. They found that the $^{13}C$ and $^{15}N$ increased significantly in tomato seedlings within 48 h after injection into the soil thus indicating that organic protein N-uptake by plants is very rapid (Tida et al., 2009).

Furthermore, Jones et al., (2005a) addressed the question of competition for amino acids between plants and microorganisms. Although molecules such as amino acids are excellent C and N sources for microbes, they can potentially out compete plant roots for free amino acids (Owen and Jones, 2001), and microbial capture of free amino acids (glycine in this case) is very rapid over a wide range of concentrations (0.1 µM-10 mM) interestingly enough plant uptake of N was maximized at high amino acid concentrations where the microbial utilization was slowest (Jones et al., 2005a).

These results indicate that protein-N can be utilized by plants rapidly in a major way for their nutritional needs in the presence of microorganisms competing for the same source of N (Jones et al., 2005a).

Endophytic bacteria colonize inner host tissues, sometimes in high numbers, without damaging the host or eliciting strong defense responses (Hurek, 2011). Prominent sites for active ingress into roots are the emergence points of lateral roots and to some extent the zone of differentiation and elongation near the root tip, where slightly disrupted or not completely differentiated tissues may facilitate penetration. Intercellular spaces in the epidermal and cortical regions and lysed plant cells are major sites of colonization, with locally high cell densities of up to $(10)^{10}$ cells/$cm^3$ (Chi et al., 2005).

Proteases are a type of extracellular depolymerases; they are released by microorganisms via three known mechanisms; i) substrate induction, ii) end-product repression or de-repression due to insufficient nutrient supply and iii) constitutive production of small amounts (Geisseler et al., 2010). Protease enzymes catalyze amide hydrolysis breaking the peptide bond and releasing individual amino acids via a proton transfer reaction (Karaman, 2011). They can therefore hydrolyze large proteins into peptides and amino acids with wide substrate specificities and can degrade most non-structural proteins (Geisseler et al., 2010).

Production of extracellular proteases is induced by the presence of substrate i.e., proteins in the medium while the presence of easily metabolizable C end products may repress enzyme production (Kalisz, 1988; Haab et al., 1990; Allison and Macfarlane, 1992). Given the abundant presence of protein organic N in soils and applied animal based manures, the microbial propensity to exude proteases, and the ability of plants to take up peptides and free amino acids we hypothesize the following pathway to supply plants N needs (see FIG. 4).

Although bacteria can colonize plants both epiphytically i.e., plant rhizosphere and endophytically in the plant apolplasts, selected endophytic bacteria because they live within the plant and can therefore recover more easily from stressful situations (Kozyrovska et al., 1996). In addition, being away from the natural biocenosis gives them a significant edge in competing with the native soil bacteria (Kozyrovska et al., 1996).

Although both bacteria and fungi produce proteases, we selected bacteria because they generally outnumber their fungal counterparts by 2-150 fold (Hilda and Fraga, 1999). In our quest for selecting the suitable organic (protein) nitrogen solubilizing bacteria we screened endophytic bacteria isolated from natural plant samples and screened them for protease production.

SUMMARY OF THE INVENTION

The proposed embodiment pertains to the development of biofertilizer consisting of protease producing endophytic bacteria (BioCat-N) inoculated crop seeds as an environmentally sustainable, and cost-effective alternative to synthetic N fertilizers and as a means of increasing the efficacy of synthetic fertilizers.

DETAILED DESCRIPTION OF PREFERRED EMBODIMENTS

Animal manure is rich in valuable macro and micro nutrients and also supplies organic matter to improve the soil's physical and chemical properties and is used in exclusion to synthetic fertilizers in organic farming.

Nitrogen in manure mainly occurs in three forms—organic, ammonia/ammonium, and nitrate of which organic N is the predominant form of N in manure (http://www.poultrywaste.okstate.edu/files/f-2228web.pdf). Similar to organic nitrogen in soils, organic nitrogen in manure also retains the potential to be depolymerized into free amino acids and oligopeptides.

Although the nutrient content of animal manure varies based on method of collection and storage, and animal species, an average nutrient content of manure is summarized in Table 1.

The object of the purported invention is to develop a biocatalyst (BioCat-N) consisting of organic N solubilizing endophytic bacteria that colonize the root and shoot of plants at sufficient inoculum density so as to facilitate adequate dissolution of organic N into oligopeptides and free amino acids that can be taken up readily by plants.

The purported invention will work by inoculating crop seeds with endophytic bacteria primed to release protease an enzyme that depolymerizes proteins and peptides to free amino acids and oligopeptides. A particular advantage of endophytic bacteria is that they do not need to compete with native soil bacteria; they should therefore be able to degrade and depolymerize the proteinaceous organic nitrogen in soils and in soil amendments (e.g., manure) in the vicinity of plant roots thus releasing free amino acids and oligopeptides for the N nutritional needs of the plant. Hence, in part, the present invention describes preparations of novel plant-derived endophytes, and the creation of synthetic combinations of seeds with heterologous plant-derived endophytes as well as the recognition that such synthetic combinations display a specific beneficial property of reducing the nitrogen fertilizer requirement of the agricultural plants newly created by the present inventors.

BioCat-N is thus purported to increase organic nitrogen availability and uptake by crops be it in fertilized or unfertilized soils.

At Biomineral Systems, we have conducted experiments with corn and sorghum and show evidence of plant growth on poultry manure alone in the complete absence of ammonium and nitrate that exceeded growth of plants growth with $NH_4^+$ and nitrate similar to synthetic fertilizers. Because of the novelty of this discovery, to the best of the inventor's knowledge no products exist that has been scientifically designed to effectively, efficiently and reliably harness this poultry manure a rich source of organic N for plant uptake and supplying the plant's nutritional needs.

Endophytic organic nitrogen solubilizing bacterial selection and evaluation as potential organic nitrogen solubilizing biocatalyst for two crops corn and sorghum is complete.

The preferred embodiment has been evaluated in crop systems in hydroponic, simulated soil systems, and real soils.

The preferred embodiment has included isolation of protease producing endophytic bacteria from plant samples of corn, sorghum, and sugarcane.

Further, the preferred embodiment has involved determining inoculation efficacy of the isolated endophytic bacteria by determining inoculum density in root and shoot of corn and sorghum.

Further, the preferred embodiment has involved using nitrogen deficiency symptoms, root/shoot ratio, and chlorophyll content measurements and demonstrating that corn and sorghum seeds inoculated with selected N solubilizing endophytic bacteria grown with insoluble organic-N species present in soils such as poultry manure performed as well or better than non-inoculated control seeds grown with full strength Hoagland solution containing dissolved inorganic nitrogen.

Definitions

'Soil nitrogen' is defined as the sum total of soil-inorganic and soil-organic nitrogen.

An 'agricultural plant' can be a monocotyledonous or a dicotyledonous plant typically used in agriculture.

A 'reference plant' is a monocotyledonous or a dicotyledonous plant typically used in agriculture that has not been synthetically inoculated by an 'endophytic bacteria' and serves as a control against which the performance of the 'host agricultural plant' to draw conclusions about the success of the invention.

REFERENCES

Allison, C., and Macfarlane, G. T., 1992. Physiological and nutritional determinants of protease secretion by Clostridium sporogenes: characterization six extracellular proteases. Applied Microbiology & Biochemistry, 37, 152-156.

Adamczyk, B., Godlewski, M., Smolander, A., and Kitunen, V., 2009. Degradation of proteins by enzymes exuded by Allium porrum roots—A potentially important strategy for acquiring organic nitrogen by plants. Plant Physiology and Biochemistry, 47, 919-925.

Ahearn, D. G., Meyers, S. P., Nichols, R. A., 1968. Extracellular proteinases of yeasts and yeast like fungi. Applied Microbiology, 16, 1370-1374.

Atwell R. C., Schulte L. A., Westphal L. M., 2010 How to build multifunctional agricultural landscapes in the US Corn Belt: Add perennials and partnerships, Land Use Policy, 27 1082-1090.

Chi F., Shen S. H., Cheng H. P., Jing Y. X., Yanni Y. G., Dazzo F. B., 2005. Ascending migration of endophytic rhizobia, from roots to leaves, inside rice plants and assessment of benefits to rice growth physiology. Applied Environmental Microbiology 2005, 71:7271-7278.

Gupta, R., Beg, Q. K., Khan, S., and Chauhan, B., 2002. An overview on fermentation, downstream processing and properties of microbial alkaline proteases. Applied Microbiology and Biotechnology, 60, 381-395.

Geisseler, D., Horwath, W. R., Joergensen, R. G., and Ludwig, B., 2010. Pathways of Nitrogen Utilization by soil microorganisms—A review. Soil Biology & Biochemistry, 42, 2058-2067.

Haab, D., Hagspiel, K., Szakmary, K., Kubicek, C. P., 1990. Formation of the extracellular proteases from Trichoderma reesei QM 9414 involved in cellulose degradation. Journal of Biotechnology, 16, 187-198.

Hilda, R., and Fraga, R., 1999. Phosphate solubilizing bacteria and their role in plant growth promotion. Biotechnology Advances, 17, 319-339.

Hinsinger, P., 2001. Bioavailability of soil inorganic P in the rhizosphere as affected by root-induced chemical changes: a review. Plant and Soil, 237, 173-195.

Hirner, A., Ladwig, F., Stransky, H., Okumoto, S., Keinath, M., Hams, A., Frommer, W. B., and Koch, W., 2006. Arabidiopsis LHT1 is a high affinity transporter for cellular amino acid uptake in both root epidermis and leaf mesophyll. The Plant Cell, 18, 1931-1946.

Hurek, B. R., and Hurek, T., 2011. Current Opinion in Plant Biology, 14:435-443

Jamtgard, S., Nasholm, T., and Kerstin, H-D., 2010. Nitrogen compounds in soil solutions of agricultural land. Soil Biology & Biochemistry, 42, 2325-2330.

Jones, D. L., Shannon, D., Junvee-Fortune, T., and Farrar, J. F., 2005. Plant capture of free amino acids is maximized under high soil amino acid concentrations. Soil Biology & Biochemistry, 37, 179-181.

Jones, D. L., and Darrah, P. R., 1994. Amino-acid influx at the soil-root interface of Zea mays and its implications in the rhizosphere. Plants and Soil, 163, 1-12.

Jones, D. L., Healey, J. R., Willette, V. B., Farrar, J. F., Hodge, A., 2005a. Dissolved organic nitrogen uptake by plants—an important N uptake pathway. Soil Biology & Biochemistry, 37, 413-423.

Jones, D. L., Shannon, D., Junvee-Fortune, T., and Farrar, J. F., 2005b. Plant capture of free amino acids is maximized under high soil amino acid concentrations. Soil Biology & Biochemistry, 37, 179-181.

Kalisz, H. M., 1988. Microbial proteinases. Advances in Biochemical Engineering/Biotechnology, 36, 1-65.

Kielland, K., 1994. Amino-acid-absorption by arctic plants-implications for plants-implications for plant nutrition and nitrogen cycling. Ecology, 75, 2373-2383.

Kraiser, T., Gras, D. E., Gutierrez, A. G., Gonzalez, B., and Gutierrez, R. A., 2011. A holistic view of nitrogen acquisition in plants. Journal of Experimental Botany, 62, 1455-1466.

Khan, S. A., Mulvaney, R. L., Ellsworth, T. R., and Boast, C. W., 2007. The myth of nitrogen fertilization for soil carbon sequestration. Journal of Environmental Quality, 36, 1821-1832.

Karaman, R., 2011. Analyzing Kemp's amide cleavage: A model for amidase enzymes. Computational and Theoretical Chemistry 963, 427-434.

Kozyrovska, N., Kovtunovych, G., and Groosova, E. Kuharchuk, P., and Kordyum, V., 1996. Novel inoculants for an environmentally-friendly crop production. Resources Conservation and Recycling, 18, 79-85.

Lee, Y. H., Foster, J., Chen, J., Voll, L. M., Weber, A. P., Tegeder, M., 2007. AAP1 transports uncharged amino acids into roots of Arabidopsis. The plant Journal, 50, 305-319.

Lipson, D., and Nasholm, T., 2001. The unexpected versatility of plants: organic nitrogen use and availability in terrestrial ecosystems. Oecologia, 128, 305-316.

Mannheim, T., Braschkat, J., and Marschner, H., 1995. Reduction of ammonia emissions after application of liquid cattle manure on arable land and grassland: Comparison of wide spread application, application in narrow bands and injection. ZEITSCHRIFT FUR PFLANZENERNAHRUNG UND BODENKUNDE, 158, 535-542.

Mulvaney, R. L., Khan, S. A., and Ellsworth, T. R., 2006. Need for a soil-based approach in managing nitrogen fertilizers for profitable corn production. Soil Science Society of America Journal, 70, 172-182.

Mulvaney, R. L., Khan, S. A., and Ellsworth, T. R., 2007. Response to "Comments on 'Need for a soil-based approach in managing nitrogen fertilizers for profitable corn production' and 'Soil organic nitrogen enrichment following soybean in an Iowa corn-soybean rotation'". Soil Science Society of America Journal, 71, 256-256.

Mulvaney, R. L., Khan, S. A., and Ellsworth, T. R., 2009. Synthetic nitrogen fertilizers deplete soil nitrogen: A global dilemma for sustainable cereal production. Journal of Environmental Quality, 38, 2295-2314.

Mulvaney, R. L., Khan, S. A., and Ellsworth, T. R., 2010a. Comments on "Synthetic Nitrogen Fertilizers Deplete Soil Nitrogen: A Global Dilemma for Sustainable Cereal Production," by R L Mulvaney, R. L., Khan, S. A., and Ellsworth, T. R., 2010b. Reply to Additional Comments on "Synthetic Nitrogen Fertilizers Deplete Soil Nitrogen: A Global Dilemma for Sustainable Cereal Production," by R L Mulvaney, S A Khan, and T R Ellsworth in the Journal of Environmental Quality 2009 38:2295-2314. Journal of Environmental Quality, 39, 1530-1532.

Näsholm, T., Ekblad, A., Nordin, A., Giesler, R., Hogberg, M., Hogberg, P., 1998. Boreal forest plants take up organic nitrogen, Nature, 392, 914-916.

Näsholm, T., Huss-Danell, K., Hogberg, P., 2001. Uptake of glycine by field grown wheat. New Phytologist, 150, 59-63.

Olczyk, T., Yuncong, L., Edward, E., Na-Lampag, S., and Fan, X., 2007. Updates on Fertilizer prices. University of Florida WAS.

Owen, A. G., Jones, D. L., 2001. Competition for amino acids between wheat roots and rhizosphere microorganisms and the role of amino acids in plant N acquisition. Soil Biol. Biochem. 33, 651-657.

Paungfoo-Lonhienne, C., Lonhienne, T. G., Rentsch, D., Robinson, N., Christies, M., Webb, R. I., Gamage, H. K., Carroll, B. J., Schenk, P. M., Schmidt, S., 2008. Plants can use protein as a nitrogen source without assistance from other organisms. Proceedings of the National Academy of Sciences USA, 105, 4524-4529.

Sanhueza, E., 1982. The role of the atmosphere in nitrogen cycling. Plant and Soil, 67, 61-71.

Schulten, H. R., and Schnitzer, M., 1997. The chemistry of soil organic nitrogen: a review. Biology and Fertility of Soils, 26, 1-15.

Svennerstam, H., Ganeteg, U., Nisholm, T., 2008. Root uptake of cationic amino acids by Arabidopsis depends on functional expression of amino acid permease 5, New Phytologist, 180, 620-630.

Stribley, D. P., Read, D. J., 1980. The biology of mycorrhiza in the Ericaceae. 7. The relationship between mycorrhizal infection and the capacity to utilize simple and complex organic nitrogen-sources. New Phytologist, 86, 365-371.

Schmidt, S., and Stewart, G. R., 1999. Glycine metabolism by plant roots and its occurrence in Australian plant communities. Australian Journal of Plant Physiology, 26, 253-264.

Sauheitl, L., Glaser, B., and Weigelt, A., 2009. Uptake of intact amino acids by plants depend on soil amino acid concentrations. Environmental and Experimental Botany, 66, 145-152.

Sommerfield, T. G., Chang, C., 1985. Changes in soil properties under annual application of feedlot manure and different tillage practices. Soil Sci. Soc. Am. J. 49, 983-988.

Tida, G. E., Song, S., Roberts, P., Jones, D. L., Huang, D., and Iwasaki, K., 2009. Environmental and Experimental Botany, 66, 357-361.

Yamagata, M., and Ae, N., 1996. Nitrogen uptake response of crops to organic nitrogen. Soil Science and Plant Nutrition, 42, 389-394.

Warren, C. R., Adams, P. R., 2007. Uptake of nitrate, ammonium and glycine by plants of Tasmanian wet eucalypt forests. Tree Physiol. 27, 413-419.

http://www.grist.org/article/series/the-n2-dilemma-is-America-fertilizing-disaster Simplified soil nitrogen cycle—http://www.ipm.iastate.edu/ipm/icm/2005/9-19/fiftydegrees.html

BRIEF DESCRIPTION OF DRAWINGS

FIG. 3: Average nitrogen analysis of types of manure

EXAMPLE 1: ISOLATING ENDOPHYTIC BACTERIA FROM FRESH PLANT SAMPLES

Figure 1:
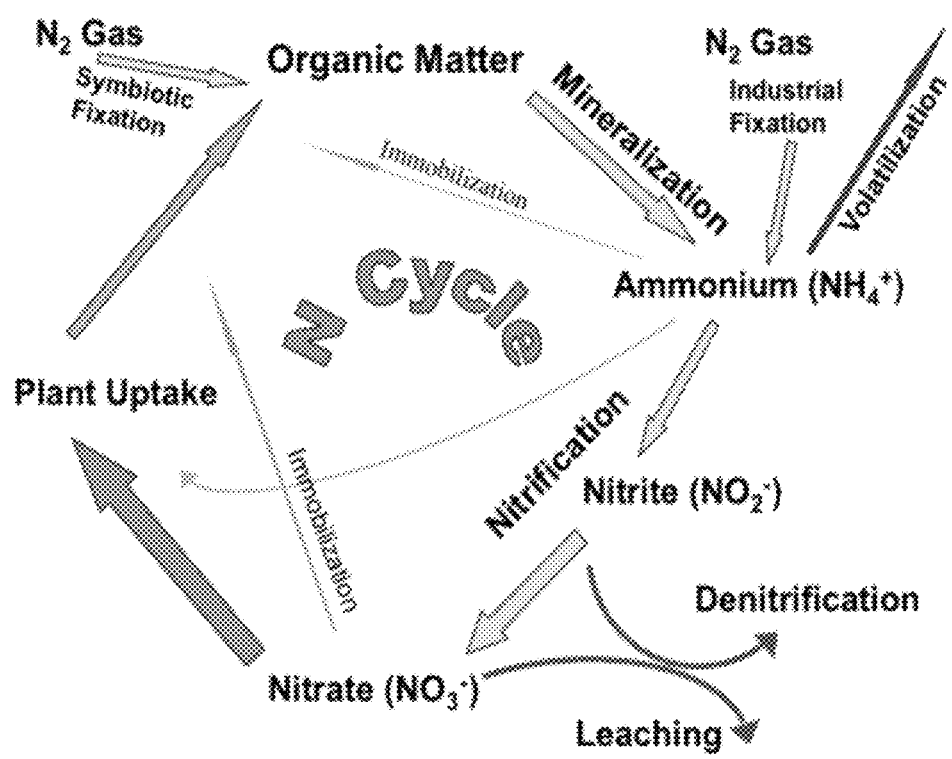
FIG. 1: A simplified view of the nitrogen cycle
Figure 2:
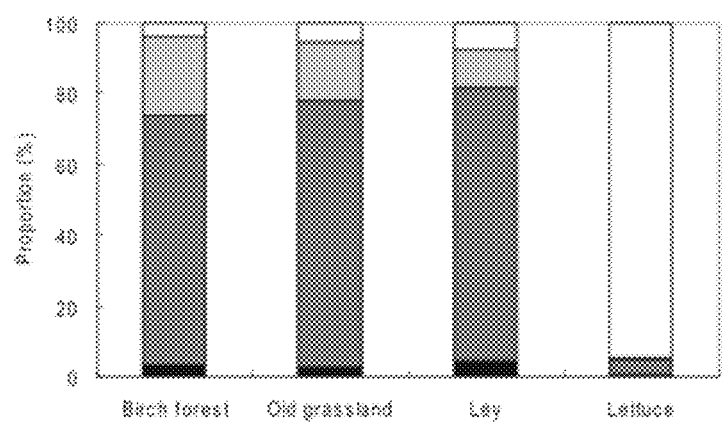
FIG. 2: Proportions of free amino acids (black bars), bound amino acids (dark grey bars), ammonium (light grey bars) and nitrate (white bars) in soil solutions adapted from Jamtgard et al., (2010).
Figure 4:
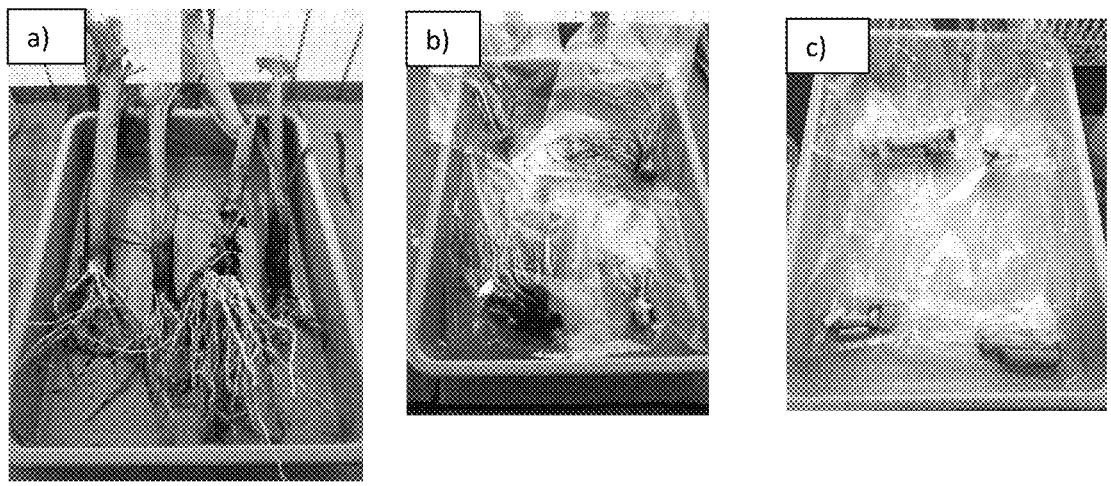
FIG. 4: Endophytic bacteria isolated from plants corn, sorghum, sugarcane: a) corn plants washed in tap water; b) separated roots and shoots; c) separated and chopped corn shoots for further surface sterilization and grinding to isolate endophytic bacteria
Figure 5:
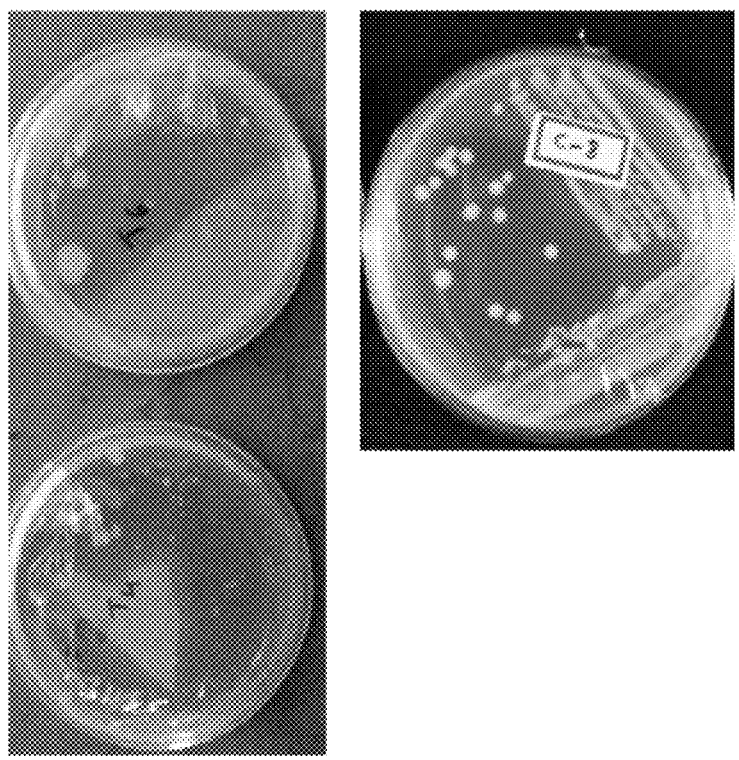
FIG. 5: Endophytic bacteria isolated from corn plants
Figure 6:
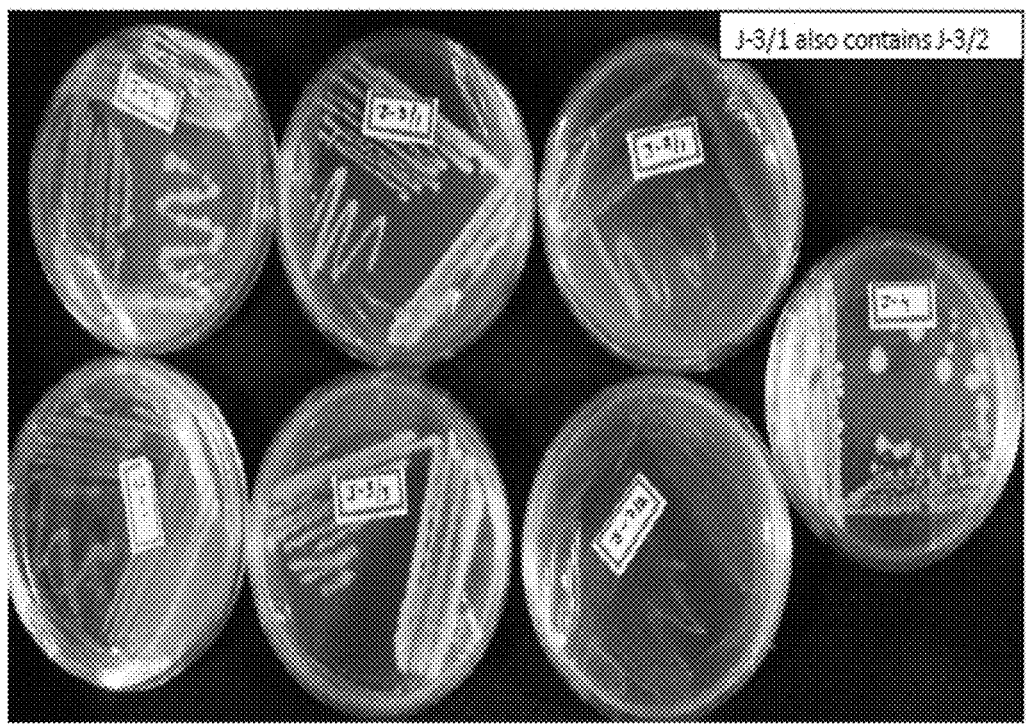
FIG. 6: Endophytic bacteria isolated from sorghum plants
Figure 7:
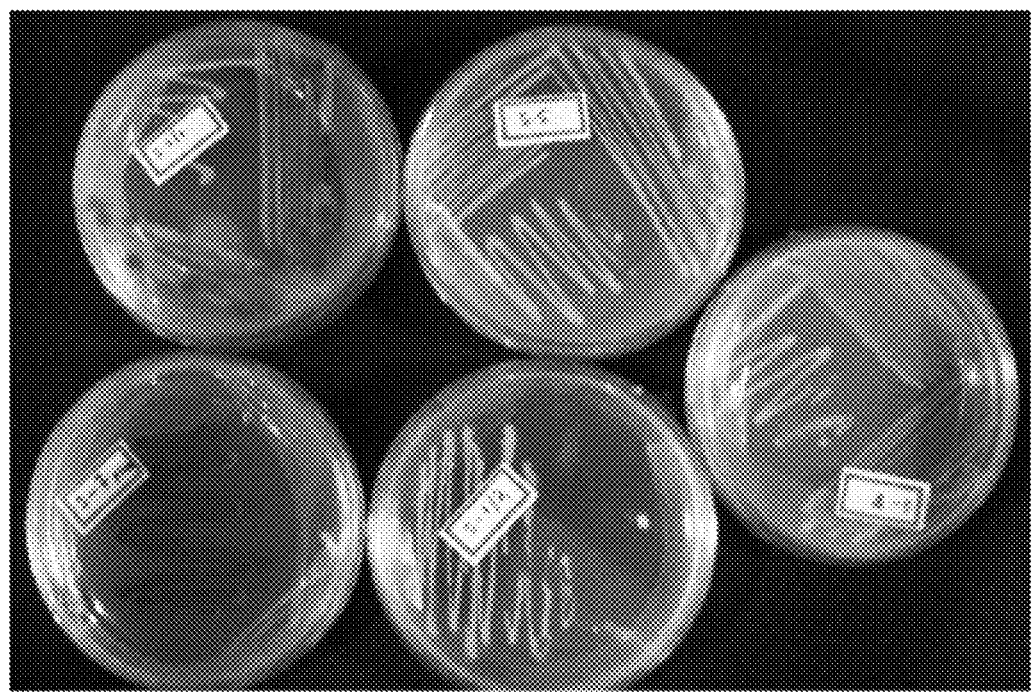
FIG. 7: Endophytic bacteria isolated from sugarcane plants
Figure 8:
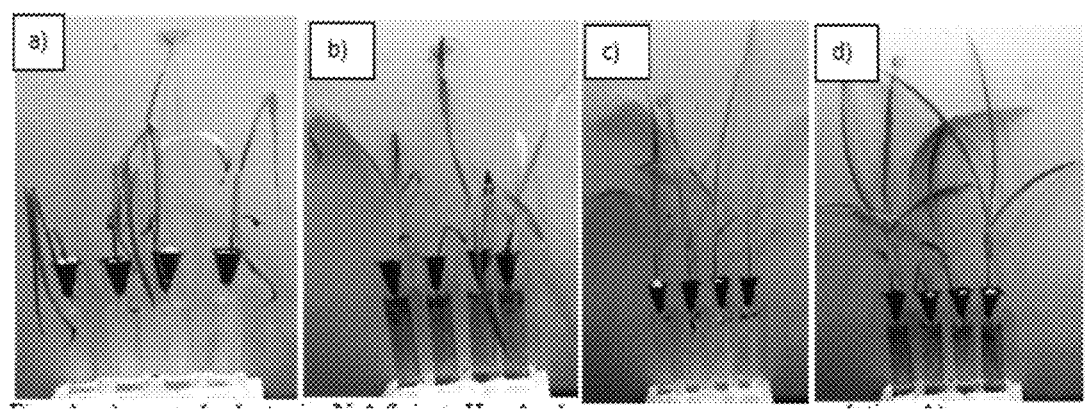
FIG. 8: a) control plants in N-deficient Hoagland solution; b) non-inoculated corn plant grown in complete Hoagland solution amended with 1 g poultry manure; c) non-inoculated corn plants grown in complete Hoagland solution; d) corn plant inoculated with j2/2 grown in N-deficient Hoagland solution amended with 1 g poultry manure.

Fresh samples of corn, sorghum, and sugarcane plants were acquired and washed in tap water. The roots and shoots from each plant was separated. The roots and shoots were separated and chopped. They were then surface sterilized to eliminate any epiphytic bacteria and to facilitate isolation of only endophytic bacteria. The samples were then ground to isolate endophytic bacteria. Endophytic bacteria isolated from corn plants included T4, T6, and C8. Endophytic bacteria isolated from sorghum plants included J-1, J-2/1, J-2/2 (BMS-101, NRRL accession #B-67826) J-3/1, J-3/2, J-3/3, and J-4. Endophytic bacteria isolated from sugarcane plants included S-1/1, S-1/2, S-5, S-7, and S-8.

EXAMPLE 2: CHARACTERIZING ACID AND ALKALINE PROTEASE PRODUCTION FROM THE ISOLATED ENDOPHYTIC BACTERIA

Acid protease assay: Protease activity was determined using the modified Anson method as described in Hashimoto et al., (1973). Briefly, reaction mixture was prepared by combining 1 ml of enzyme solution and 5 ml of bovine casein in 0.05 M acetate buffer (pH 2.5) and incubated at 30 degree C. for 10 minutes. Five ml of 0.11 M trichloroacetic acid was added to stop the reaction. The reaction mixtures was filtered after incubation at 30 degree C. for 30 minutes. Five ml of 0.55 M sodium carbonate was added to 2 ml of the filtrate followed by the addition of 1 ml of thrice diluted phenol reagent. Acid protease activity exuded by endophytic bacteria was quantified based on the concentration of tyrosine measured at 660 nm.

Alkaline protease assay: Alkaline protease activity was determined according to the procedure of Smita et al., (2012). The assay medium (50 ml) containing nutrient broth and 1% casein at pH 10 was inoculated with each isolate and incubated at 37 degree C. for 48 hrs in a water bath shaker. After incubation, the broth cultures were centrifuged at 10,000 rpm for 10 minutes at 4 degree C. and the supernatant was collected to determine the activity of alkaline protease. The activity of alkaline protease was determined similar to the procedure described above for acid protease by measuring the release of tyrosine at 280 nm. The main difference was that the pH was adjusted to pH 10 instead of 2.5 by addition of Glycine-NaOH buffer.

Because Acid-protease are very effective at the common soil pHs we selected J2/2 (BMS-101, NRRL accession #B-67826) an endophytic bacteria isolated from sorghum and tested its inoculation efficacy in corn and sorghum.

TABLE 2

| Endophytic bacteria isolated from corn (C, T), surgarcane (S) and sorghum (J) | Concentration of Tyrosine produced (µg/ml) as an estimation of acid protease activity |
|---|---|
| J3/1 | 159.4 |
| S-7P | 66 |
| J2/2 (BMS-101, NRRL accession # B-67826) | 126 |
| S-1/2 | 55.7 |
| J-4 | 112.6 |
| T-4 | 24.8 |
| T-6 | 18.5 |
| S-8 | 46.4 |
| S-7 | 54 |
| S-5 | 58.4 |
| S-1/12 | 42.8 |
| J2/1 | 102.6 |
| J-3/3 | 52.6 |
| J-1 | 94 |
| C-8 | 44.9 |

TABLE 3

| Endophytic bacteria isolated from corn (C, T), surgarcane (S) and sorghum (J) | Concentration of Tyrosine produced (µg/ml) as an estimation of alkaline protease activity |
|---|---|
| S-1/2 | 77 |
| S-8 | 89 |
| S-7 P | 97 |
| S-1/3 | 87 |

EXAMPLE 3: TESTING INOCULATION EFFICACY OF ENDOPHYTIC BACTERIA

The inoculum for endophytic bacteria was grown under controlled conditions for 48 hrs to inoculum density of $10_8$ to $10_{10}$ cfu/ml. The inoculum was centrifuged and suspended in sterile PBS to a concentration of $10_8$ cfu/ml. The seeds were surface sterilized with 95% ethanol for 2 min and 2.5% sodium hypochlorite for 20-30 min followed by washing seven times in sterile water. Surface sterilized seeds were soaked in sterile PBS containing endophytic bacteria and placed in a temperature controlled incubator shaker at 25 degree C. for exactly 30 minutes. The inoculated seeds were washed with 70% alcohol for 2 minutes and with 2% sodium hypochlorite followed by washing with sterile water 5 times. The surface sterilized seeds were placed in sterile petriplates containing 0.7% of water agar, 5-10 seeds per plate. The seed containing plates were transferred to growth chamber set at 30 degree C. and left for 48 hours to germinate. Well germinated seeds with shoot and roots were separated and surface sterilize with 95% of ethanol for 5 min and 20 min with 4% sodium hypochlorite followed by 4-5 times sterile water rinse. The water rinsed root and shoot parts were transferred to PBS containing solution and ground to rapture the tissue. 1 ml of ground tissue was diluted in 9 ml of sterile water serial dilutions were continued to obtain 100 and 1000 fold dilution and spread on nutrient agar plates. After growth the colonies were counted and tabulated. Non-inoculated seeds served as negative controls.

Based on the amounts of protease production J3/1 and J2/2 (BMS-101, NRRL accession #B-67826) were selected for testing their inoculation efficacy in corn and sorghum. Because J3/1 inoculum density measurements in roots and shoot replicates showed wide variability, J2/2 (BMS-101, NRRL accession #B-67826) was chosen as the protease producing strain for further experiments. The non-inoculated control seeds showed zero inoculum density in the root and shoots.

TABLE 4

Inoculation efficacy of endophytic bacteria in corn and sorghum

| Sample description | cfu/ml (calculated using 1000 fold dilution) |
|---|---|
| J2/2 (BMS-101, NRRL accession # B-67826) inoculum density in corn root | $2.4 \times 10^6$ |
| J2/2 (BMS-101, NRRL accession # B-67826) inoculum density in corn shoot | $3.1 \times 10^5$ |
| J2/2 (BMS-101, NRRL accession # B-67826) inoculum density in sorghum root | $6.6 \times 10^6$ |
| J2/2 (BMS-101, NRRL accession # B-67826) inoculum density in sorghum shoot | $1.8 \times 10^6$ |

Un-inoculated corn and sorghum seeds showed zero inoculum density in roots and shoots Un-Inoculated Corn and Sorghum Seeds Showed Zero Inoculum Density in Roots and Shoots

EXAMPLE 4

Standard Hoagland solutions (hydroponic nutrient solutions) were prepared according to the composition in (ref) and contained $Ca(NO_3)_2.4H_2O$, $NH_4NO_3$, $KCl$, $KNO_3$, $Mg(NO_3)_2.6H_2O$, $KH_2PO_4$, $Fe(NO_3)_3.9H_2O$, Na HEDTA, $MnCl_2.4H_2O$, $H_3BO_3$, $ZnSO_4.7H_2O$, $CuSO_4.5H_2O$, and $Na_2MoO_4.2H_2O$. The young corn seedlings cannot tolerate full strength Hoagland solution. Hence 1/2 strength Hoagland solution was used from VE to V1 vegetative stage. The plants were grown until V3 vegetative growth stage because nitrogen deficiency symptoms can be observed during V1 to V3 growth stage. Nitrogen deficient Hoagland solution was prepared by eliminating all sources of nitrates and ammonium nitrogen and contained $CaCl_2)_2.2H_2O$, KCl, $K_2SO_4$, $MgCl_2.6H_2O$, $KH_2PO_4$, $FeCl_3.6H_2O$, Na HEDTA, $MnCl_2.4H_2O$, $H_3BO_3$, $ZnSO_4.7H_2O$, $CuSO_4.5H_2O$, and $Na_2MoO_4.2H_2O$. Poultry manure was added at the rate of g/L.

The viable inoculated seeds were placed in a muslin cloth and washed with running tap water and dried by placing on autoclaved tissue paper. The seeds were surface sterilized in laminar flow hood with 70% alcohol for 30 minutes and then by washing with 10% sodium hypochlorite solution for 20 minutes. After surface sterilization, the seeds were washed with sterile water, excess water removed by blotting with autoclaved tissue paper, and then air dried under laminar flow Five to ten surface sterilized and dried seeds were then placed in sterile petriplates containing water soaked blotting paper and transferred to growth chamber maintained at 25-27 degree C. and left for 48 hours to germinate. After seeds germinated, they were transferred to hydroponic reactors. Hydroponic reactors constituted of root permeable plastic buckets. Air pump with air controllers were used to provide aeration to the plants in hydroponic systems and all systems were maintained under greenhouse conditions at a temperature of 24±2 degree C. and relative humidity of 70±3%. After control plants showed nitrogen deficiency symptoms, the plants were removed from hydroponic reactors and washed under running tap water to completely remove Hoagland solution. The plant was dried with blotting paper while taking care to not damage the roots.

Reduced leaf area and degradation of chlorophyll in leaves is symptomatic of nitrogen deficiency so we measured chlorophyll a and chlorophyll b in plants. A single leaf per plant was used for obtaining 10 leaf discs of 1 cm each and weighed. Five of these leaf discs were placed per tube containing 5 ml of 1:1 ratio of DMSO:acetone and the tubes were placed in the dark overnight to allow chlorophyll leaching. After chlorophyll leaching the solution turns green and the concentration of chlorophyll in leaves is calculated by measuring absorbance at 645, and 663 nm. The total chlorophyll is estimated using the following formulae:

$$\text{Chlorophyll } II\ a(g/l) = 0.0127\ A_{663} - 0.00269\ A_{645}$$

$$\text{Chlorophyll } II\ b\ (g/l) = 0.0029\ A_{663} - 0.00468\ A_{645}$$

$$\text{Total Chlorophyll } (g/l) = 0.0202\ A_{663} + 0.00802\ A_{645}$$

What is claimed is:

1. A method for synthetically and systemically reducing nitrogen fertilizer requirement in any plant growth medium by purified homologous or heterologous endophytic bacteria producing protease enzymes, sufficient to satisfy crop needs for optimal yields in said plant growth medium by colonizing the plant root and shoot at sufficient inoculum density that consists essentially of the following steps: 1) growing an endophytic bacteria having the ability to produce acid protease enzyme, and alkaline protease enzyme to inoculum density of 108 to 1010 cfu/ml; 2) suspending the said inoculum in sterile phosphate buffer saline medium to a concentration of 108 cfu/ml thereby providing an endophytic inoculum; 3) preparing the corn, sorghum, wheat, rice, and other vegetable, fruit, flower or grass seeds or plant parts by surface sterilizing with 95% ethanol for 2 min and 2.5% sodium hypochlorite for 20-30 min followed by washing seven times in sterile water; 4) soaking the aforementioned surface sterile seeds or plant parts in the said endophytic inoculum of step 2; 5) henceforth placing in a temperature controlled incubator at 25 degree C. for exactly 30 minutes with or without gentle shaking at 40-80 rpm, then washing the thus prepared inoculated seeds or plant part with 70% alcohol for 2 minutes and with 2% sodium hypochlorite followed by washing with sterile water 5 times; 6) treating the said prepared seeds or plant parts of step 5 with other seed treatments and coatings; 7) drying the said seed of step 6 before planting; and 8) planting the said prepared seeds or the said plant part in a plant growth medium with less than the recommended nitrogen fertilizer amount wherein the nitrogen is applied as urea, anhydrous ammonia, urea ammonium nitrate, ammonium nitrate, manure based fertilizers, composted fertilizers, high N— bat guano, single cell based proteins or another form.

2. The method of claim 1, wherein the inoculated plant, plant part or seed is introduced in a plant growth medium in an amount effective to increase the yield of plants grown in said plant growth medium.

3. The method of claim 1, in which said endophytic inoculum, is introduced into a plant growth medium as part of an inoculant composition comprising at least $1 \times 10^5$ colony forming units of said endophytic inoculum per gram or per milliliter of inoculant composition.

4. The method of claim 1, in which said endophytic inoculum, is introduced into a plant growth medium as part of a treated plant part.

5. The method of claim 4, in which said treated plant part comprises at least 1×10$^5$ colony forming units of said endophytic inoculum per kilogram of plant part.

6. The method of claim 1, in which said endophytic inoculum is introduced into a plant growth medium at a rate of at least 1×10$^5$ colony forming units of said endophytic inoculum per acre of plant growth medium.

7. The method of claim 1 wherein said endophytic inoculum is applied to plant seeds, one year before said plant seed is planted in a plant growth medium.

8. The method of claim 1 wherein a formulation containing said endophytic inoculum comprises at least one member selected from the group consisting of an agriculturally compatible carrier, a tackifier, a microbial stabilizer, a fungicide, an antibacterial agent, an herbicide, a nematicide, an insecticide, a plant growth regulator, a rodenticide, and a nutrient.

9. The method of claim 1 wherein said endophytic inoculum comprises the ability to induce in the agricultural plant production of protease enzyme.

10. The method of claim 1 wherein the endophytic bacteria is obtainable from interior or exterior of the agricultural plant.

11. The method of claim 1 wherein the endophytic bacteria is obtainable from a different cultivar, variety or crop as compared to the seed.

12. The method of claim 1 wherein the inoculation of endophytic bacteria in step 4 comprises spraying, immersing, coating, encapsulating, injecting or dusting the seeds with a formulation containing said endophytic inoculum and at least one member selected from the group consisting of an agriculturally compatible carrier, a tackifier, a microbial stabilizer, a fungicide, an antibacterial agent, an herbicide, a nematicide, an insecticide, a plant growth regulator, a rodenticide, and a nutrient.

13. The method of claim 1 wherein the purified endophytic bacteria comprises a plurality of seed bacterial endophyte entities.

14. The method of claim 1 wherein the purified endophytic bacteria is combined with a purified fungal population.

15. A method comprising using NRRL B 67826 that is heterologous to the seed for the purpose of reducing nitrogen fertilizer requirement for optimal plant growth and yield in organic and conventional agriculture compared to a reference agricultural plant grown under the same conditions with no reduction in nitrogen fertilizer that includes the following steps: 1) growing NRRL B 67826 having the ability to produce acid protease enzyme, and alkaline protease enzyme to a specific inoculum density of 108 to 1010 cfu/ml; 2) suspending the said inoculum in sterile phosphate buffer saline medium to a concentration of 108 cfu/ml thereby providing an endophytic inoculum; 3) preparing the vegetable, fruit, flower, or grass seed, or plant parts by surface sterilizing with 95% ethanol for 2 min and 2.5% sodium hypochlorite for 20-30 min followed by washing seven times in sterile water; 4) soaking the aforementioned seed or or plant parts in the said endophytic inoculum; and 5) henceforth placing in a temperature controlled incubator at 25 degree C. or any other temperature dependent on seed type or plant parts with or without gentle shaking at 40-80 rpm for exactly 30 minutes, then washing the thus prepared inoculated seeds or plant parts with 70% alcohol for 2 minutes and with 2% sodium hypochlorite followed by washing with sterile water 5 times; 6) treating the said prepared seeds or plant parts of step 5 with other seed treatments and coatings; 7) drying the said seed of step 6 before planting; and 8) planting the said prepared seeds or the said plant part in a plant growth medium with less than the recommended nitrogen fertilizer amount wherein the nitrogen is applied as urea, anhydrous ammonia, urea ammonium nitrate, ammonium nitrate, manure based fertilizers, composted fertilizers, high N— bat guano, single cell based proteins or another form.

16. The method of claim 1 in which said endophytic inoculum when applied to the said plant seed or plant growth medium can reduce or eliminate leaching of the applied nitrogen fertilizer in conventional and organic agriculture.

17. The method of claim 10 wherein NRRL B 67826 when applied to the said plant seed or plant growth medium can reduce or eliminate leaching of the applied nitrogen fertilizer in conventional and organic agriculture.

18. The method of claim 10 wherein the inoculated plant, plant part or seed is introduced in a plant growth medium to increase yield with optimal growth.

19. The method of claim 10, in which the said strain NRRL B 67826 is introduced into a plant growth medium as part of an inoculant composition comprising at least 1×10$^5$ colony forming units of NRRL B 67826 per gram or per milliliter of inoculant composition.

20. The method of claim 10, in which the said strain NRRL B 67826 is applied to the said plant seed one year before the said plant seed is planted in a plant growth medium.

* * * * *